US009850469B2

(12) United States Patent
Smith, III et al.

(10) Patent No.: US 9,850,469 B2
(45) Date of Patent: Dec. 26, 2017

(54) METHODS OF STAPLING AND UNSTAPLING PEPTIDES AND PROTEINS

(71) Applicant: The Trustees Of The University Of Pennsylvania, Philadelphia, PA (US)

(72) Inventors: Amos B. Smith, III, Merion, PA (US); Stephen Brown, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 14/659,754

(22) Filed: Mar. 17, 2015

(65) Prior Publication Data

US 2015/0376579 A1 Dec. 31, 2015

Related U.S. Application Data

(60) Provisional application No. 61/954,203, filed on Mar. 17, 2014.

(51) Int. Cl.
 *C07K 1/113* (2006.01)
 *C12N 9/02* (2006.01)
 *C07K 7/54* (2006.01)

(52) U.S. Cl.
 CPC .......... *C12N 9/0051* (2013.01); *C07K 1/1133* (2013.01); *C07K 1/1136* (2013.01); *C07K 7/54* (2013.01)

(58) Field of Classification Search
 None
 See application file for complete search history.

(56) References Cited

U.S. PATENT DOCUMENTS

2011/0172392 A1* 7/2011 Kajihara .............. C07K 1/1077
 530/322

OTHER PUBLICATIONS

Yin ('Constrained Peptides as Miniature Protein Structures' ISRN Biochemistry vol. 2012, 15 pages).*
Abdo et al, "Design, Synthesis, and Photochemical Validation of Peptide Linchpins Containing the S,S-Tetrazine Phototrigger", Organic Letters, Jul. 6, 2012, 14(13), 3518-3521.
Asplund et al, "Two-Dimensional Infrared Spectroscopy of Peptides by Phase-Controlled Femtosecond Vibrational Photon Echoes", Proceedings of the National Academy of Sciences in the United States of America, Jul. 18, 2000, 97(15), 8219-8224.
Bock et al, "Getting in Shape: Controlling Peptide Bioactivity and Bioavailability Using Conformational Constraints", ACS Chemical Biology, Mar. 15, 2013, 8(13), 488-499.
Blackman et al, "Tetrazine Ligation: Fast Bioconjugation Based on Inverse-Electron-Demand Diels-Alder Reactivity", Journal of the American Chemical Society, Oct. 15, 2008, 130(41), 13518-13519.
Brown, S.P. and Smith, III, A.B., "Peptide/Protein Stapling and Unstapling: Introduction of s-Tetrazine, Photochemical Release, and Regeneration of the Peptide/Protein", Journal of the American Chemical Society, Apr. 1, 2015, 137(12), 4034-4037.
Carboni, R A.; and Lindsey, R V., "Reactions of Tetrazines with Unsaturated Compounds. A New Synthesis of Pyridazines", Journal of the American Chemical Society, Aug. 1959, 81(16), 4342-4346.
Catsimpoolas, N.; and Wood, J. L., "The Reaction of Cyanide with Bovine Serum Albumin", Journal of Biological Chemistry, Dec. 1964, 239(12), 4132-4137.
Catsimpoolas, N.; and Wood, J. L., "Specific Cleavage of Cystine Peptides by Cyanide", Journal of Biological Chemistry, Apr. 25, 1966, 241(8), 1790-1796.
Courter et al, "The Design and Synthesis of Alanine-Rich α-Helical Peptides Constrained by an S,S-Tetrazine Photochemical Trigger: A Fragment Union Approach", Journal of Organic Chemistry, Dec. 20, 2013, 759-768.
Collins et al, "In Situ Conjugation of Dithiophenol Maleimide Polymers and Oxytocin for Stable and Reversible Polymer-Peptide Conjugates", Bioconjugate Chemical, Mar. 5, 2015, 26(4), 633-638.
De Araujo et al, "Comparative α-Helicity of Cyclic Pentapeptides in Water", Angewandte Chemie, International Edition in English, Jul. 1, 2014, 53(27), 6965-6969.
Degani et al, "Selective Cyanylation of Sulfhydryl Groups", Journal of the American Chemical Society, Nov. 18, 1970, 92(23), 6969-6971.
Dawson et al, "Synthesis of Proteins by Native Chemical Ligation", Science, Nov. 4, 1994, 266(5186), 776-779.
Dellinger et al, "Laser Induced Isotope Enrichment in a Rare Gas Matrix", Journal of the American Chemical Society, Apr. 1977, 99(9), 3197-3198.
Ellman, G. L., "Tissue Sulfhydryl Groups", Archives of Biochemistry Biophysics, May 1959, 82(1), 70-77.
Gasparini et al, "Cellular Uptake of Substrate-Initiated Cell-Penetrating Poly(disulfide)s", Journal of the American Chemical Society, Apr. 15, 2014, 136(16), 6069-6074.
Gongora-Benitez et al, "Multifaceted Roles of Disulfide Bonds. Peptides as Therapeutics", Chemical, Reviews, Jan. 22, 2014, 114(2), 901-926.
Haney, C. M. and Horne, W. S., "Oxime Side-Chain Cross-Links in an α-Helical Coiled-Coil Protein: Structure, Thermodynamics, and Folding-Templated Synthesis of Bicyclic Species", Chemistry-European Journal, Aug. 19, 2013, 19(34), 11342-11351.
Hruby et al, "Emerging Approaches in the Molecular Design of Receptor-Selective Peptide Ligands: Conformational, Topographical and Dynamic Considerations", Biochemical Journal, Jun. 1, 1990, 268(2), 249-262.
Hruby et al, "Conformational and Topographical Considerations in Designing Agonist Peptidomimetics from Peptide Leads", Current Medicinal Chemistry, Sep. 2000, 7(9), 945-970.

(Continued)

*Primary Examiner* — Karlheinz R Skowronek
*Assistant Examiner* — Ronald Niebauer
(74) *Attorney, Agent, or Firm* — Baker & Hostetler LLP

(57) ABSTRACT

The present disclosure pertains to the field peptide stapling and/or macrocyclization, where a structural motif is used to improve the properties of amino acid sequences (e.g. protease resistance, cellular penetration, biological activity). Also within the scope of the disclosure are methods for unstapling the S,S-tetrazine-containing amino acid sequence. The disclosure is also directed to methods for the reductive removal of thiocyanates from an amino acid sequence with cysteine to recycle back to the native amino acid sequence.

15 Claims, 5 Drawing Sheets

(56) References Cited

OTHER PUBLICATIONS

Jeng et al, "High-Resolution Solution Structures of Oxidized and Reduced *Escherichia coli* Thioredoxin", Structure, Sep. 15, 1994, 2(9), 853-868.
Kawamoto et al, "Design of Triazole-Stapled BCL9 α-Helical Peptides to Target the β-Catenin/B-cell CLL/lymphoma 9 (BCL9) Protein-Protein Interaction", Journal of Medicinal Chemistry, Feb. 9, 2012, 55(3), 1137-1146.
Kessler, H., "Conformation and Biological Activity of Cyclic Peptides", Angewandte Chemie, International Edition in English, Jul. 1982, 21(7), 512-523.
Kim et al, "Synthesis of All-Hydrocarbon Stapled A-Helical Peptides by Ring-Closing Olefin Metathesis", Nature Protocols, May 2011, 6, 761-771.
Lau et al, "Peptide Stapling Techniques Based on Different Macrocyclisation Chemistries", Chemical Society Reviews, Jan. 7, 2015, 44(1), 91-102.
Lang et al, "Genetic Encoding of Bicyclononynes and Trans-Cyclooctenes for Site-Specific Protein Labeling in Vitro and in Live Mammalian Cells Via Rapid Fluorogenic Diels-Alder Reactions", Journal of the American Chemical Society, Jun. 27, 2012, 134(25), 10317-10320.
Marsault, E. and Peterson, M.L., "Macrocycles Are Great Cycles: Applications, Opportunities, and Challenges of Synthetic Macrocycles in Drug Discovery", Journal of Medicinal Chemistry, Mar. 7, 2011, 54(7), 1961.
Schafmeister et al, "An All-Hydrocarbon Cross-Linking System for Enhancing the Helicity and Metabolic Stability of Peptides", Journal of the American Chemical Society, Jun. 2000, 122, 5891.
Schieber et al, "Conjugation of Transferrin to Azide-Modified CdSe/ZnS Core-Shell Quantum Dots using Cyclooctyne Click Chemistry", Angewandte Chemie International Edition, Oct. 2012, 51(42), 10523-10527.
Selvaraj, R; and Fox, J.M., "Trans-Cyclooctene—A Stable, Voracious Dienophile for Bioorthogonal Labeling", Current Opinion in Chemical Biology, Oct. 2013,17(5),753-760.
Smith, "Protein Modification, Bioconjugation, and Disulfide Bridging Using Bromomaleimides", Journal of the American Chemical Society, Jan. 21, 2010, 132(6), 1960-1965.
Spokoyny et al, "A Perfluoroaryl-Cysteine SNAr Chemistry Approach to Unprotected Peptide Stapling", Journal of the American Chemical Society, Apr. 24, 2013, 135(16), 5946-5949.
Tucker et al, "Di-cysteine S,S-tetrazine: A Potential Ultra-Fast Photochemical Trigger to Explore the Early Events of Peptide/Protein Folding", Journal of Photochemistry and Photobiology A: Chemistry, Apr. 15, 2012, 234, 156-163.
Tucker et al, "Nonequilibrium Dynamics of Helix Reorganization Observed by Transient 2D IR Spectroscopy", Proceedings of the National Academy of Sciences of the United States of America, Oct. 22, 2013, 110(43), 17314-17319.
Tucker et al, "Tetrazine Phototriggers: Probes for Peptide Dynamics", Angewandte Chemie International Edition, May 10, 2010, 49(21), 3612-3616.
Veber et al, "Conformationally Restricted Bicyclic Analogs of Somatostatin", Proceedings of the National Academy of. Sciences of the United States of America, Jun. 1, 1978, 75(6), 2636-2640.
Veber et al, "Highly Active Cyclic and Bicyclic Somatostatin Analogues of Reduced Ring Size", Nature, Aug. 9, 1979, 280(5722), 512-514.
Veber et al, "A Potent Cyclic Hexapeptide Analogue of Somatostatin", Nature, Jul. 2, 1981, 292, 55-58.
Verdine, "All-Hydrocarbon Stapled Peptides as Synthetic Cell-Accessible Mini-Proteins", Drug Discovery Today Technologies, Spring 2012, 9(1), e41-e47.
Walensky, L. D. and Bird, G. H., "Hydrocarbon-Stapled Peptides: Principles, Practice, and Progress", Journal of Medicinal Chemistry, Feb. 19, 2014, 57(15), 6275-6288.
White, C.J. and Yudin, A.K., "Contemporary Strategies for Peptide Macrocyclization", Nature Chemistry, Jun. 23, 2011, 3(7), 509-524.
Wu et al, "Development and Evaluation of 18F-TTCO-Cys40-Exendin-4: A PET Probe for Imaging Transplanted Islets", Journal of Nuclear Medicine, Feb. 2013, 54(2), 244-251.
Zhang et al, "Peptides-Staple Method Development and Its Application in Cancer Therapy", Current Medicinal Chemistry, Jul. 2014, 21(21), 2438-2452.

* cited by examiner

SEQUENCE LISTING

```
<160> NUMBER OF SEQ ID NOS: 9

<210> SEQ ID NO 1
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ala Gly Cys Lys Asn Phe Phe Trp Lys Thr Phe Thr Ser Cys
1               5                   10

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Glu Cys Ser Cys Lys
1               5

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Val Cys Asp Pro Cys Ala
1               5

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4
```

Tyr Cys Gly Gly Gly Cys Ala Leu
1               5

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: hCys
<220> FEATURE:
<221> NAME/KEY: MOD_RES
<222> LOCATION: (6)..(6)
<223> OTHER INFORMATION: hCys

<400> SEQUENCE: 5

Tyr Cys Gly Gly Gly Cys Ala Leu
1               5

<210> SEQ ID NO 6
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ala Ala Ala Ala Cys Ala Ala Ala Cys Ala Ala Ala Ala
1               5                   10

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ile Cys Tyr Gly Gly Phe Met Cys Ala
1               5

<210> SEQ ID NO 8
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

His Cys Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Cys
            20                  25                  30

<210> SEQ ID NO 9
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 9

Ile Thr Phe Cys Asp Leu Leu Cys Tyr Tyr Gly Lys Lys Lys
1               5                   10
```

METHODS OF STAPLING AND UNSTAPLING PEPTIDES AND PROTEINS

CROSS-REFERENCE TO RELATED APPLICATIONS

This application claims the benefit of the priority of U.S. Provisional Patent Application No. 61/954,203, filed Mar. 17, 2014, which application is incorporated by reference herein.

SEQUENCE LISTING

The instant application contains a Sequence Listing which has been submitted electronically in ASCII format and is hereby incorporated by reference in its entirety. Said ASCII copy, created on Aug. 31, 2015, is named 103241.006033-14-7077_SL.txt and is 2,670 bytes in size.

GOVERNMENT RIGHTS

This invention was made with government support under Grant No. P 41 GM 104605 awarded by the National Institutes of Health. The government has certain rights in the invention.

BACKGROUND

Peptide and protein conformations comprise one of the principal determinates of biofunction and bioavailabilty. The ability to induce or restrict peptide/protein conformation and thereby reduce polarity, increase proteolytic stability, and/or improve drugability, peptide/protein macrocyclization has become an effective, well recognized tactic. ((a) Marsault, E.; Peterson, M. L. Journal of Medicinal Chemistry 2011, 54, 1961-2004. (b) White, C. J.; Yudin, A. K. Nature Chemistry 2011, 3, 509-524.)

The development of an all hydrocarbon-stapling tactic has provided a number of bioactive peptides, locked into their active conformation, to target intracellular protein-protein interactions. Alternative examples of helix stabilization include side chain tethering of peptides/proteins with amides, triazoles or oximes linkages. Spokoyny and co-workers recently employed perfluoroarylation to stabilize α-helical conformations between two cysteine residues, resulting in enhanced cell permeability and increased chemical stability. (Spokoyny, A. M., et al. J. Am. Chem. Soc. 2013. 135, 5946-5949.). Methods to readily insert a staple and to remove an inserted staple—without severely disrupting the peptide/protein—are needed.

SUMMARY

The present disclosure is directed to processes for preparing an S,S-tetrazine moiety comprising contacting an aqueous solution of an amino acid sequence comprising two proximal cysteine residues or two proximal homocysteine residues with an organic solution comprising a di-halo-tetrazine for a time sufficient to form the S,S-tetrazine moiety. The disclosure is also directed to processes for preparing an amino acid sequence having two proximal cysteine residues or two proximal homocysteine residues comprising contacting an amino acid sequence comprising two proximal thiocyanate moieties with cysteine for a time sufficient to produce the amino acid sequence comprising proximal cysteine residues or the amino acid sequence comprising two proximal homocysteine residues.

The disclosure is further directed to processes comprising preparing an S,S-tetrazine moiety comprising contacting an aqueous solution of an amino acid sequence comprising two proximal cysteine residues or two proximal homocysteine residues with an organic solution of a di-halo-tetrazine for a time sufficient to form the S,S-tetrazine moiety; irradiating the S,S-tetrazine moiety with light to form an amino acid sequence comprising two proximal thiocyanate moieties; and contacting the amino acid sequence comprising two proximal thiocyanate moieties with cysteine for a time sufficient to produce the amino acid sequence comprising proximal cysteine residues or the amino acid sequence comprising two proximal homocysteine residues.

BRIEF DESCRIPTION OF THE DRAWINGS

FIGS. 2b-2e disclose SEQ ID NOS: 3-6, respectively, in order of appearance. FIGS. 2g-2i disclose SEQ ID NOS: 7, 1 and 8, respectively, in order of appearance.

FIG. 3 discloses SEQ ID NOS 3-5, 9 and 1, respectively, in order of appearance.

DETAILED DESCRIPTION OF ILLUSTRATIVE EMBODIMENTS

Figure 1:
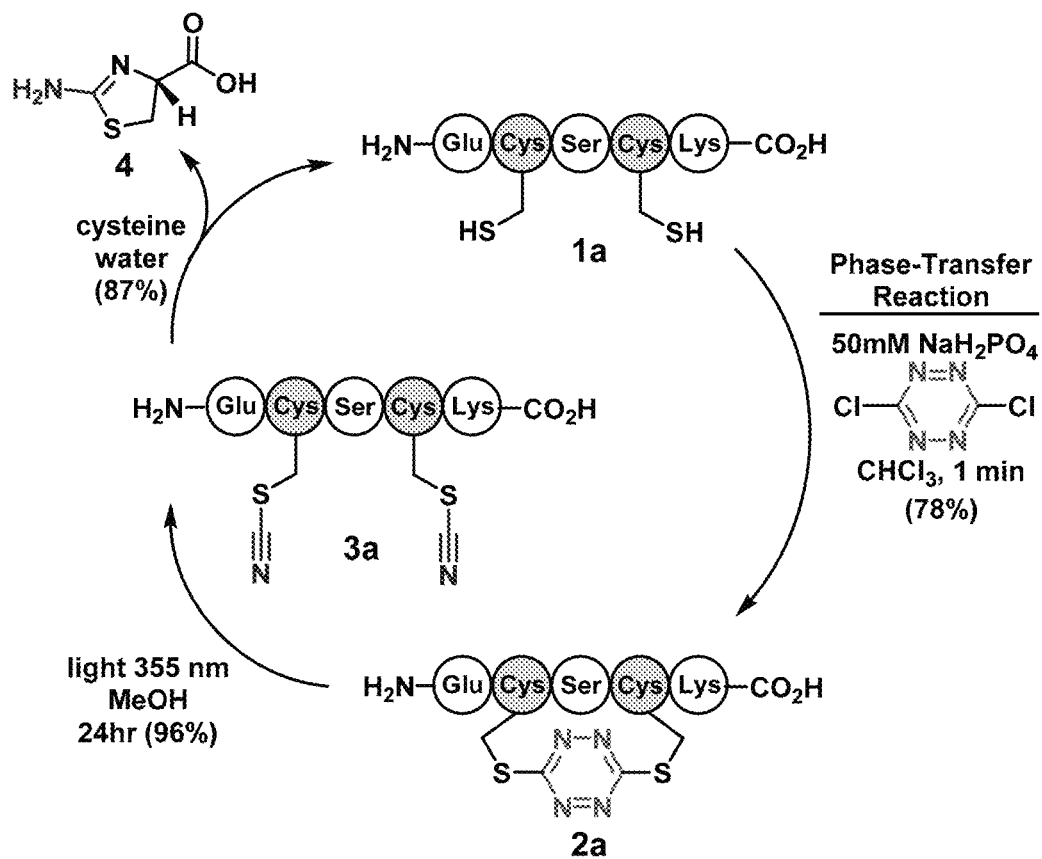
FIG. 1 depicts a preferred reaction sequence of the disclosure (SEQ ID NO: 2).

The disclosure is directed to the preparation of S,S-tetrazine-containing amino acid sequences, preferably using a phase-transfer reaction medium. The phase-transfer reaction medium used in the present disclosure is a significant improvement over the solid-phase peptide synthesis (SPPS) methods previously disclosed for preparing S,S-tetrazine moieties. For example, the phase-transfer methods of the disclosure enable the rapid incorporation of the s-tetrazine chromophore into unprotected peptides and proteins possessing two proximal cysteines or two proximal homocysteine residues (or a cysteine residue proximal to a homocysteine residue). Moreover, while SPPS attempts to incorporate an s-tetrazine chromophore into peptides possessing arginine side-chains led to decomposition, the phase-transfer methods of the disclosure allow for the incorporation of the s-tetrazine chromophore into peptides possessing both reactive arginine and methionine side-chains without decomposition.

The disclosure is directed to processes for preparing an S,S-tetrazine moiety using a phase-transfer reaction system. Phase transfer reaction systems include two phases—one phase being an aqueous solution and the other being an organic solution. The two phases are not completely miscible within each other such that two separate phases can be present in the reaction vessel during the reaction.

The S,S-tetrazine moieties of the disclosure are within an amino acid sequence. Preferred amino acid sequences of the disclosure include peptides, proteins, and protein fragments.

The processes of the disclosure comprise contacting an aqueous solution of an amino acid sequence that comprises two proximal cysteine residues or two proximal homocysteine residues. In alternate embodiments, the aqueous solution comprises an amino acid sequence that comprises a cysteine residue proximal to a homocysteine residue. As used herein, "proximal" refers to the closeness in space of moieties within an amino acid sequence of the disclosure. When used in referring to proximal cysteine residues, for example, the cysteine residues are sufficiently close enough to each other in space such that they can react with a di-halo-tetrazine to form an S,S-tetrazine moiety. For example the cysteine residues, homocysteine residues, or a combination thereof, can be separated by 0 to 35 amino acid residues, for example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 amino acid residues, in the amino acid sequences of the disclosure. Preferably, the residues are separated by 1, 2, 3, 4, 5, 10, or 27 amino acid residues. More preferably, the residues are separated by 1 amino acid residue. In another embodiment, the residues are separated by 2 amino acid residues. Alternatively, the residues are separated by 3 amino acid residues. In some embodiments, the residues are separated by 4 amino acid residues. In other embodiments, the residues are separated by 5 amino acid residues. Preferably, the residues are separated by 10 amino acid residues. Alternatively, the residues are separated by 27 amino acid residues.

The incorporation of the tetrazine moiety into a variety of peptides possessing various spacings (i, i+2–i+28) between the cysteine/homocysteine residues was investigated to test the compatibility with amino acid sequences including coded as well as D-amino acids. The term "tetrazine moiety" as used herein refers to any moiety having a tetrazinyl group and may be attached to a peptide using known techniques, as well as those described herein.

To this end, stapled tetrazine macrocycles can be prepared employing the phase-transfer protocol described herein and were isolated using reverse-phase chromatography. Only minor amounts of disulfide and dimeric products are observed, when using the described methods.

The aqueous solution of the amino acid sequence comprising two proximal cysteine residues or two proximal homocysteine residues or a cysteine residue proximal to a homocysteine residue is a water-based solution. In addition to containing the amino acid sequence comprising the two proximal residues, the aqueous solution can include buffers to control the pH of the aqueous solution. In preferred embodiments, the pH of the aqueous solution comprising the amino acid sequence comprising the two proximal residues is between about 2 and 9. For example, the pH can be 2 or 3. Alternatively, the pH can be between about 5 and about 9. Preferably, the pH is about 5. Buffers that can provide a particular pH are known in the art, per se. Preferred buffers for use in the disclosure include, for example, phosphate buffers. One preferred phosphate buffer is monosodium phosphate. Another preferred buffer is a guanidine salt buffer, for example, guanidine hydrochloride.

In the processes of the disclosure, the aqueous solution of the amino acid sequence comprising two proximal cysteine residues or two proximal homocysteine residues or a cysteine residue proximal to a homocysteine residue is contacted with an organic solution of a di-halo tetrazine. Preferred di-halo-tetrazines include dichlorotetrazine, dibromotetrazine, diiodotetrazine, and difluorotetrazine. A particularly preferred di-halo-tetrazine is dichlorotetrazine.

An organic solvent that can dissolve the di-halo-tetrazine and that can form a two-phase reaction system with the aqueous solution can be used within the scope of the disclosure. Preferred solvents include chloroform, ethyl acetate, diethyl ether, toluene, dichloromethane, cyclohexane, and combinations thereof. One preferred organic solvent is chloroform. In selecting a solvent for use in the disclosure, those solvents having a solubility in water of less than 10 g/100 mL at 20° C. are particularly useful.

In the processes of the disclosure, the aqueous solution of the amino acid sequence comprising two proximal cysteine residues or two proximal homocysteine residues or a cysteine residue proximal to a homocysteine residue is contacted with an organic solution of a di-halo tetrazine. The contacting step can be achieved via any means known in the art, including stirring, shaking, and vortexing. The contacting step can be performed at ambient temperature. Alternatively, the contacting step can be performed at elevated temperatures greater than 25° C.

After an aqueous solution of the amino acid sequence comprising two proximal cysteine residues or two proximal homocysteine residues or a cysteine residue proximal to a homocysteine residue has contacted an organic solution comprising the di-halo-tetrazine for a time sufficient to form the S,S-tetrazine moiety, for example, up to 1 minute, up to 5 minutes, up to 15 minutes, up to 30 minutes, up to 60 minutes, or longer than 60 minutes, the two phases can be separated. The S,S-tetrazine moiety will be present in the aqueous phase. Lyophilization of the aqueous phase provides the isolated S,S-tetrazine moiety.

If desired, the isolated S,S-tetrazine moiety can be purified using any of the methods known in the art, for example, reverse-phase HPLC (high performance liquid chromatography).

In a further embodiment, the tetrazine moiety can be functionalized by one or more probes. Probes are known in the art and include dyes, for example, dyes containing fluorescein ("fluorescein dye"). In yet another embodiment, the tetrazine moiety is substituted by a fluorescein dye.

In some embodiments of the disclosure, the S,S-tetrazine moieties of the disclosure can be functionalized by subjecting the S,S-tetrazine moiety to reaction conditions known by those skilled in the art. For example, tetrazines are known in the art to participate in inverse electron demand Diels-Alder reactions by reaction of the tetrazine with a compound comprising a triple bond, for example, 5((2-aminoethyl) carbamoyl)-2-(6-hydroxy-3-oxo-3H-xanthen-9-yl)benzoic acid, or a derivative thereof

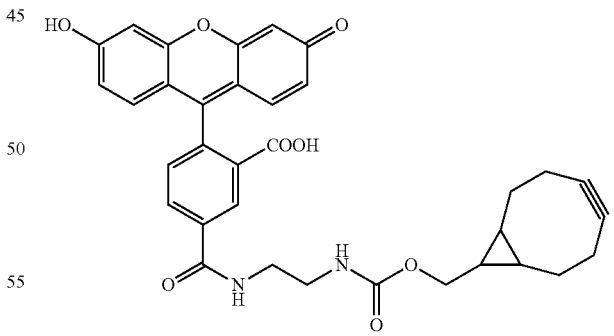

5((2-aminoethyl)carbamoyl)-2-(6-hydroxy-3-oxo-3H-xanthen-9-yl)benzoic acid See, e.g., Scheme 5.

In functionalizing the S,S-tetrazine moieties of the disclosure, probes, e.g., photophysical probes, can be incorporated into the peptides, proteins, and protein fragments of the disclosure. One example of a photophysical probes is fluorescein-based dye such as compound 5. Other biologically-relevant probes are also envisioned for use in the present disclosure.

Figure 3:
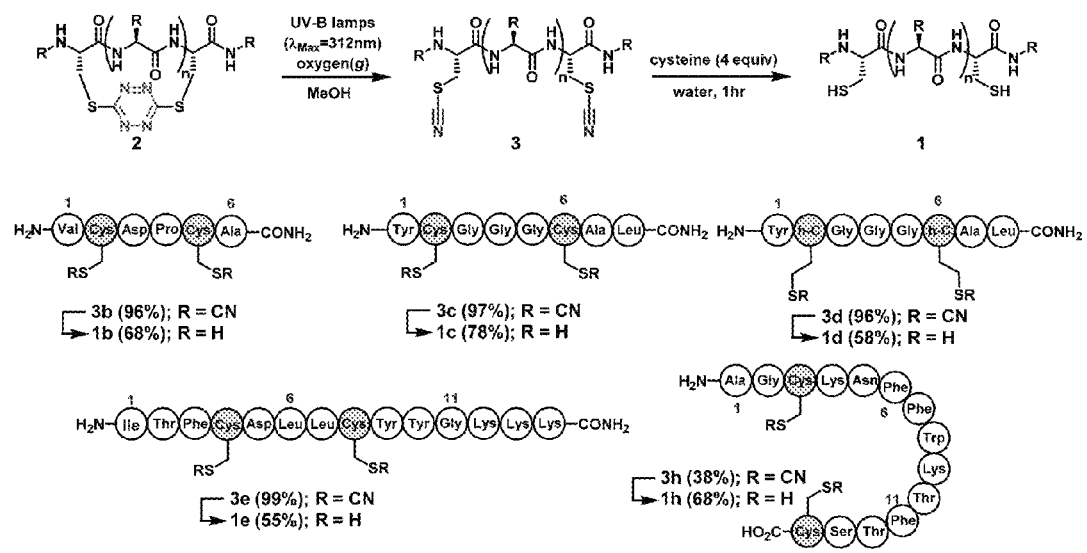
FIG. 3 depicts photochemical unstapling of several preferred embodiments of the disclosure.

The S,S-tetrazine-containing amino acid sequence produced according to the disclosure can be converted to the corresponding di-thiocyanate-containing amino acid sequence using methods known in the art. For example, the S,S-tetrazine compound can be irradiated with light, for example, irradiated with UV-B light (e.g., 355 nm) or UV-A light (e.g., 410 nm). Upon irradiation, the S,S-tetrazine decomposes to produce nitrogen and the corresponding di-thiocyanate-containing amino acid sequence. See FIGS. 1 and 3.

To demonstrate the removal of an S,S-tetrazine chromophore to achieve unstapling, tetrazine peptides 2b-e, 3h (FIG. 3) were subjected to steady-state irradiation (355 nm). Dithiocyanate peptides 3b-e, 3h were isolated in modest to good yields.

Also within the scope of the disclosure are processes for preparing an amino acid sequence having two proximal cysteine residues or two proximal homocysteine residues or a cysteine residue proximal to a homocysteine residue. These methods comprise contacting an amino acid sequence comprising two proximal thiocyanate moieties with cysteine.

Some embodiments of the disclosure comprise processes for preparing an amino acid sequence having two proximal cysteine residues or two proximal homocysteine residues or a cysteine residue proximal to a homocysteine residue comprising contacting an amino acid sequence comprising two thiocyanate moieties with cysteine for a time sufficient to produce an amino acid sequence comprising two proximal cysteine residues or two proximal homocysteine residues or a cysteine residue proximal to a homocysteine residue. The contacting step can be performed at ambient temperature. Alternatively, the contacting step can be performed at elevated temperatures greater than 25° C.

Figure 4:
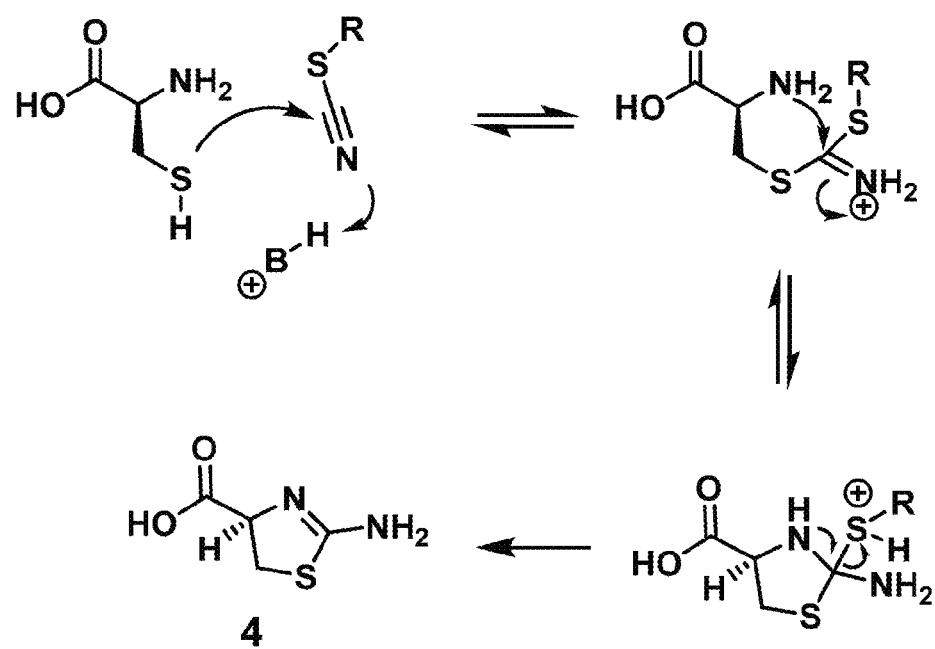
FIG. 4 depicts a proposed mechanism of the conversion of thiocyanate to thiol using cysteine.

One proposed mechanism for the conversion of a thiocyanate moiety to a cysteine moiety using cysteine is set forth in FIG. 4.

The amino acid sequence comprising two proximal thiocyanate moieties contacts cysteine for a time sufficient to produce the amino acid sequence comprising proximal cysteine residues or proximal homocysteine residues or a cysteine residue proximal to a homocysteine residue, for example, up to 30 minutes, up to 60 minutes, up to 2 hours, up to 3 hours, or up to 24 hours.

The di-thiocyanate-containing amino acid sequence can be prepared using the methods described herein or by any other method in the art.

The two proximal thiocyanate moieties of the disclosure are within an amino acid sequence. Preferred amino acid sequences of the disclosure include peptides, proteins, and protein fragments.

Preferred processes of this embodiment include contacting an amino acid sequence comprising two proximal thiocyanate moieties with cysteine. Preferably, the thiocyanate moieties are separated by 1 amino acid residue. In another embodiment, the thiocyanate moieties are separated by 2 amino acid residues. Alternatively, the thiocyanate moieties are separated by 3 amino acid residues. In some embodiments, the thiocyanate moieties are separated by 4 amino acid residues. In other embodiments, the thiocyanate moieties are separated by 5 amino acid residues. Preferably, the thiocyanate moieties are separated by 10 amino acid residues. Alternatively, the thiocyanate moieties are separated by 27 amino acid residues. In some embodiments of the disclosure, the proximal thiocyanate moieties are the by-products of the decomposition of an S,S-tetrazine moiety.

In some embodiments, the processes for preparing an amino acid sequence having two proximal cysteine residues or two proximal homocysteine residues or a cysteine residue proximal to a homocysteine residue occur in aqueous solution. While the processes preferably occur in aqueous solution, some organic solvent can be added to the aqueous solution to improve solubility of the reactants or products.

Preferably, the processes for preparing an amino acid sequence having two proximal cysteine residues or two proximal homocysteine residues or a cysteine residue proximal to a homocysteine residue occur in aqueous solution having a basic pH. A basic pH can be achieved using methods known in the art, for example, by adding buffers or by adding a source of —OH ions, for example, by adding a solution of NaOH or KOH.

Other embodiments of the disclosure are directed to processes comprising preparing an S,S-tetrazine moiety comprising contacting an aqueous solution of an amino acid sequence comprising two proximal cysteine residues or two proximal homocysteine residues with an organic solution comprising a di-halo-tetrazine for a time sufficient to form the S,S-tetrazine moiety; irradiating the S,S-tetrazine moiety with light to form an amino acid sequence comprising two proximal thiocyanate moieties; and contacting the amino acid sequence comprising two proximal thiocyanate moieties with cysteine for a time sufficient to produce the amino acid sequence comprising two proximal cysteine residues or the amino acid sequence comprising two proximal homocysteine residues.

In yet other embodiments, the processes of the disclosure comprise preparing an S,S-tetrazine moiety comprising contacting an aqueous solution of an amino acid sequence comprising a cysteine residue proximal to a homocysteine residue with an organic solution comprising a di-halo-tetrazine for a time sufficient to form the S,S-tetrazine moiety; irradiating the S,S-tetrazine moiety with light to form an amino acid sequence comprising two proximal thiocyanate moieties; and contacting the amino acid sequence comprising two proximal thiocyanate moieties with cysteine for a time sufficient to produce the amino acid sequence comprising a cysteine residue proximal to a homocysteine residue.

In these processes, an amino acid sequence comprising two proximal cysteine residues or two proximal homocysteine residues or a cysteine residue proximal to a homocysteine residue is converted to an amino acid sequence comprising an S,S-tetrazine moiety. The amino acid sequence comprising the S,S-tetrazine moiety is converted to an amino acid sequence comprising two proximal thiocyanate moieties. The amino acid sequence comprising two proximal thiocyanate moieties is converted to the amino acid sequence comprising two proximal cysteine residues or two proximal homocysteine residues or a cysteine residue proximal to a homocysteine residue, i.e., the amino acid sequence comprising two proximal thiocyanate moieties is converted to the original—or native—amino acid sequence.

In these processes of the disclosure, the S,S-tetrazine moiety is prepared using a phase-transfer reaction system. Phase transfer reaction systems include two phases—one phase being an aqueous solution and the other being an organic solution. The two phases are not completely miscible within each other such that two separate phases are present in the reaction vessel during the reaction.

The S,S-tetrazine moieties of the disclosure are within an amino acid sequence. Preferred amino acid sequences of the disclosure include peptides, proteins, and protein fragments.

The processes of comprise contacting an aqueous solution of an amino acid sequence that comprises two proximal cysteine residues or two proximal homocysteine residues or a cysteine residue proximal to a homocysteine residue. Preferably, the residues are separated by 1 amino acid residue. In another embodiment, the residues are separated by 2 amino acid residues. Alternatively, the residues are separated by 3 amino acid residues. In some embodiments, the residues are separated by 4 amino acid residues. In other embodiments, the residues are separated by 5 amino acid residues. Preferably, the residues are separated by 10 amino acid residues. Alternatively, the residues are separated by 27 amino acid residues.

The aqueous solution of the amino acid sequence comprising two proximal cysteine residues or two proximal homocysteine residues or a cysteine residue proximal to a homocysteine residue is a water-based solution. In addition to containing the amino acid sequence comprising two proximal cysteine residues or two proximal homocysteine residues or a cysteine residue proximal to a homocysteine residue, the aqueous solution can include buffers to control the pH of the aqueous solution. In preferred embodiments, the pH of the aqueous solution comprising the amino acid sequence comprising the two proximal residues is between about 2 and 9. For example, the pH can be 2 or 3. Alternatively, the pH can be between about 5 and about 9. Preferably, the pH is about 5. Buffers that can provide a particular pH are known in the art, per se. Preferred buffers for use in the disclosure include, for example, phosphate buffers. One preferred phosphate buffer is monosodium phosphate. Another preferred buffer is a guanidine salt buffer, for example, guanidine hydrochloride.

In the processes of the disclosure, the aqueous solution of the amino acid sequence comprising two proximal cysteine residues or two proximal homocysteine residues or a cysteine residue proximal to a homocysteine residue is contacted with an organic solution comprising a di-halo-tetrazine. Preferred di-halo-tetrazines include dichlorotetrazine, dibromotetrazine, diiodotetrazine, and difluorotetrazine. A particularly preferred di-halo-tetrazine is dichlorotetrazine.

An organic solvent that can dissolve the di-halo-tetrazine and that can form a two-phase reaction system with water can be used within the scope of the disclosure. Preferred solvents include chloroform, ethyl acetate, diethyl ether, toluene, dichloromethane, cyclohexane, and combinations thereof. One preferred organic solvent is chloroform. In selecting a solvent for use in the disclosure, those solvents having a solubility in water of less than 10 g/100 mL at 20° C. are particularly useful.

In the processes of the disclosure, the aqueous solution of the amino acid sequence comprising two proximal cysteine residues or two proximal homocysteine residues or a cysteine residue proximal to a homocysteine residue is contacted with an organic solution of a di-halo tetrazine. The contacting step can be achieved via any means known in the art, including stirring, shaking, and vortexing. The contacting step can be performed at ambient temperature. Alternatively, the contacting step can be performed at elevated temperatures greater than 25° C.

After the aqueous solution of the amino acid sequence comprising two proximal cysteine residues or two proximal homocysteine residues or a cysteine residue proximal to a homocysteine residue has contacted the organic solution comprising the di-halo-tetrazine for a time sufficient to form the S,S-tetrazine moiety, for example, up to 1 minute, up to 5 minutes, up to 15 minutes, up to 30 minutes, up to 60 minutes, or longer than 60 minutes, the two phases can be separated. The S,S-tetrazine moiety will be present in the aqueous phase. Lyophilization of the aqueous phase provides the isolated S,S-tetrazine moiety.

If desired, the isolated S,S-tetrazine moiety can be purified using any of the methods known in the art, for example reverse phase HPLC.

The S,S-tetrazine-containing amino acid sequence produced according to the disclosure is converted to a corresponding di-thiocyanate-containing amino acid sequence using methods known in the art. For example, the S,S-tetrazine compound can be irradiated with light, for example, irradiated with UV-A (e.g., 410 nm) light or UV-B (e.g., 355 nm) light. Upon irradiation, the S,S-tetrazine moiety decomposes to produce nitrogen and the corresponding di-thiocyanate-containing amino acid sequence. See FIGS. 1 and 3.

The amino acid sequence comprising two proximal thiocyanate moieties contacts cysteine for a time sufficient to produce the amino acid sequence comprising the two proximal cysteine residues, the amino acid sequence comprising two proximal homocysteine residues, or the amino acid sequence comprising a cysteine residue proximal to a homocysteine residue, for example, up to 30 minutes, up to 60 minutes, up to 2 hours, up to 3 hours, or up to 24 hours. The contacting step can be performed at ambient temperature. Alternatively, the contacting step can be performed at elevated temperatures greater than 25° C.

The processes of the disclosure further comprise contacting an amino acid sequence comprising two proximal thiocyanate moieties with cysteine. Preferably, the thiocyanate moieties are separated by 1 amino acid residue. In another embodiment, the thiocyanate moieties are separated by 2 amino acid residues. Alternatively, the thiocyanate moieties are separated by 3 amino acid residues. In some embodiments, the thiocyanate moieties are separated by 4 amino acid residues. In other embodiments, the thiocyanate moieties are separated by 5 amino acid residues. Preferably, the thiocyanate moieties are separated by 10 amino acid residues. Alternatively, the thiocyanate moieties are separated by 27 amino acid residues. In some embodiments of the disclosure, the proximal thiocyanate moieties are the by-products of the decomposition of an S,S-tetrazine moiety.

In some embodiments, the processes for preparing an amino acid sequence having two proximal cysteine residues or two proximal homocysteine residues or a cysteine residue proximal to a homocysteine residue occur in aqueous solution. While the processes preferably occur in aqueous solution, some organic solvent can be added to the aqueous solution to improve solubility of the reactants or products.

Preferably, the processes for preparing an amino acid sequence having two cysteine residues or two proximal homocysteine residues or a cysteine residue proximal to a homocysteine residue occur in aqueous solution having a basic pH. A basic pH can be achieved using methods known in the art, for example, by adding buffers or by adding a source of —OH ions, for example, by adding a solution of NaOH or KOH.

Amino acid residues used in the present disclosure may be recited by their full name or by reference to either the three letter or single letter amino acid code.

As used herein, the term "staple" refers to the introduction of an S,S-tetrazine moiety into a peptide or protein between two cysteine sulfhydryls, two homocysteine sulfhydryls, or a cysteine sulfhydryl and a homocysteine sulfhydryl.

As used herein, the term "unstaple" refers to the removal of an S,S-tetrazine moiety from an amino acid sequence.

As used herein, an "amino acid sequence" refers to two or more amino acids linked together through amide (peptide) bonds. Preferably, the amino acid sequences used in the disclosure include at least 4 amino acid residues. In other embodiments, the amino acid sequences used in the disclosure include at least 6 amino acid residues. Within the scope of the disclosure, amino acid sequences include non-functional amino acid chains, peptides, proteins, and protein fragments.

The following examples are merely for illustrative purposes and are not meant to limit the scope of the appended claims in any way.

EXAMPLES

Example 1: General Phase-Transfer Protocol for Tetrazine Insertion

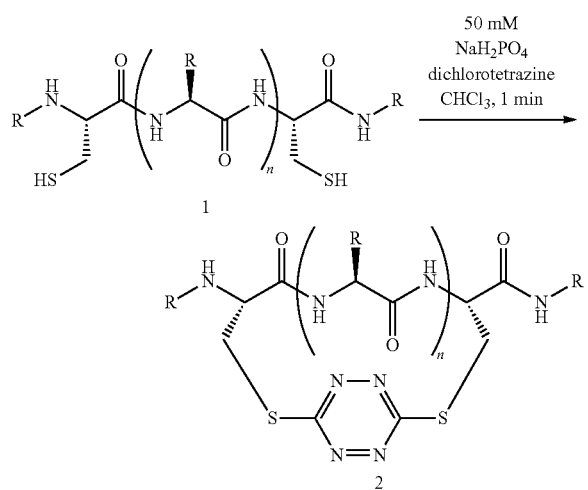

A 50 mL glass vial, was charged with unprotected peptide 1 (20 μmol) then sealed with a septum and purged with argon. Next, a degassed solution of 50 mM (pH ~5) monosodium phosphate (20 mL) was added followed by a solution of dichlorotetrazine (9.1 mg, 60 μmol, 3 equiv) in CHCl$_3$ (20 mL). The two-phases were mixed vigorously on a vortex for 1 minute. The mixture was divided between three 20 mL Falcon tubes then transferred to a benchtop centrifuge and further separated at 2500 RPM for 1 minute. The aqueous phase, now orange in color, was collected and each organic layer was extracted with an additional portion of water (5 mL) then transferred to a benchtop centrifuge and separated again at 2500 RPM for 1 minute. All of the aqueous fractions were combined and lyophilized. The crude mixture was then purified by reverse-phase high-pressure liquid chromatography (HPLC) to yield an orange powder after lyophilization.

Example 2: Guanidine Hydrochloride Method

A 20 mL glass vial, was charged with unprotected peptide 1i (5 μmol) then sealed with a septum and purged with argon. Next, a degassed solution of 6M guanidine hydrochloride in 200 mM (pH ~5) monosodium phosphate (5 mL) was added followed by a solution of dichlorotetrazine (2.3 mg, 15 μmol, 3 equiv) in CHCl$_3$ (5 mL). The two-phases were mixed vigorously on a vortex for 1 minute. The mixture was transferred to a 20 mL Falcon tubes then separated on a benchtop centrifuge at 2500 RPM for 1 minute. The aqueous phase, now orange in color, was collected and the organic layer extracted with an additional portion of water (5 mL), transferred to a benchtop centrifuge and separated again at 2500 RPM for 1 minute. All of the aqueous fractions were combined and transferred to dialysis tubing where equilibration occurred over 24 hours, the solution was then lyophilized. The crude mixture was purified by reverse-phase high-pressure liquid chromatography (HPLC) to yield 2i as an orange powder after lyophilization.

Example 3

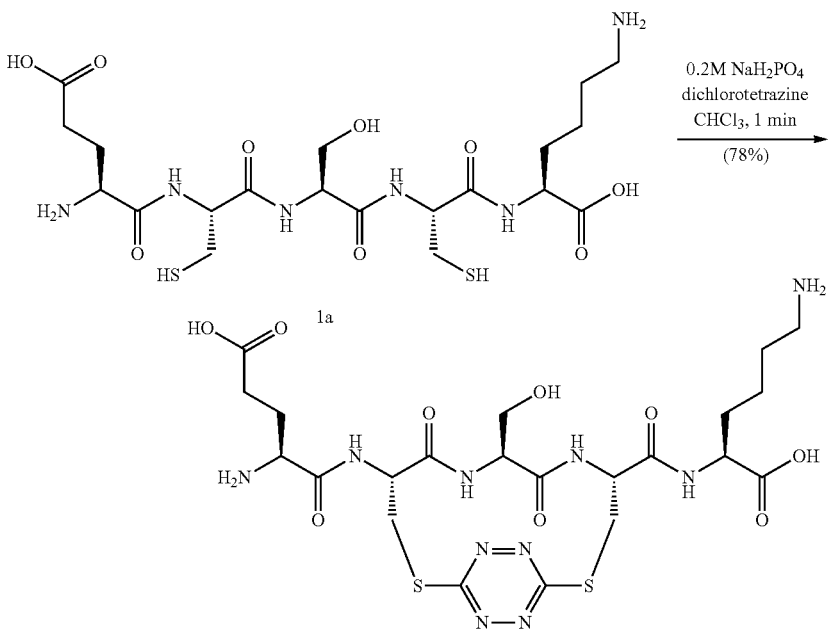

A 50 mL glass vial, was charged with unprotected peptide 1a (11.4 mg, 20 μmol) then sealed with a septum and purged with argon. Next, a degassed solution of 50 mM (pH ~5) monosodium phosphate (20 mL) was added followed by a solution of dichlorotetrazine (9.1 mg, 60 μmol, 3 equiv) in CHCl$_3$ (20 mL). The two-phases were mixed vigorously on a vortex for 1 minute. The mixture was divided between three 20 mL Falcon tubes then transferred to a benchtop centrifuge and further separated at 2500 RPM for 1 minute. The aqueous phase, now orange in color, was collected and each organic layer was extracted with an additional portion of water (5 mL) then transferred to a benchtop centrifuge and separated again at 2500 RPM for 1 minute. All of the aqueous fractions were combined and lyophilized. The crude mixture was then purified by reverse-phase high-pressure liquid chromatography (HPLC) (gradient 5-15% organic over 5 min) to yield 10.1 mg of 2a (78%) an orange powder after lyophilization. $^1$H NMR (500 MHz, D$_2$O) δ ppm 1.36 (quin, J=7.80 Hz, 2H) 1.58-1.66 (m, 3H) 1.68 (q, J=7.90 Hz, 2H) 1.79 (ddd, J=13.90, 8.30, 5.50 Hz, 1H) 1.78 (ddd, J=13.25, 8.10, 5.30 Hz, 1H) 2.07 (q, J=7.34 Hz, 2H) 2.39 (dd, J=7.30, 5.10 Hz, 1H) 2.39 (dd, J=9.80, 7.40 Hz, 1H) 2.93 (t, J=7.48 Hz, 9H) 3.50 (dd, J=15.60, 4.06 Hz, 3H) 3.54 (dd, J=18.20, 6.20 Hz, 1H) 3.57 (dd, J=11.30, 7.70 Hz, 1H) 4.10 (t, J=6.52 Hz, 1H) 4.14 (dd, J=8.44, 5.24 Hz, 1H) 4.20 (dd, J=7.10, 6.40 Hz, 1H) 4.53 (dd, J=15.39, 2.99 Hz, 1H) 4.56 (dd, J=15.60, 4.92 Hz, 1H) 4.80 (t, J=3.42 Hz, 1H) 4.99 (dd, J=4.90, 1.90 Hz, 1H). $^{13}$C NMR (126 MHz, D$_2$O) δ 178.6, 178.1, 171.7, 170.6, 170.5, 169.9, 169.1, 169.1, 61.8, 55.0, 53.9, 52.4, 52.3, 51.5, 39.1, 31.4, 31.1, 30.7, 30.2, 26.7, 26.2, 22.1. HRMS (ES) found m/z 647.2026 [(M+H)$^+$; calcd for C$_{22}$H$_{35}$N$_{10}$O$_9$S$_2$: 647.2024].

Figure 2:
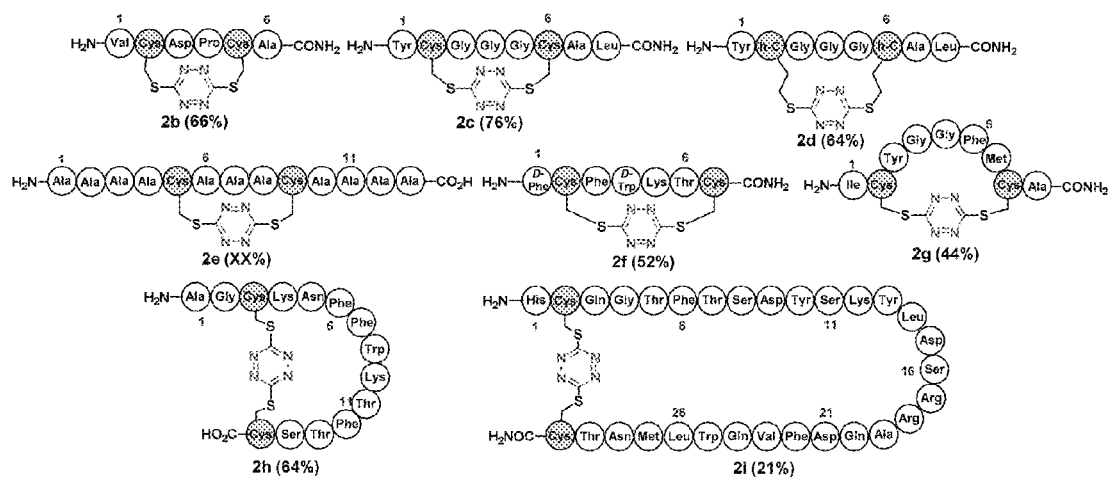
FIG. 2 depicts preferred amino-acid sequences comprising an S,S-tetrazine moiety prepared according to methods of the disclosure.

The reaction conditions set forth in Example 1 are generally applicable to a variety of amino acid sequences. See, e.g., FIG. 2. Mild acidic conditions (pH 5) were slightly favored in the reaction, with the rate of tetrazine insertion somewhat slower at low pH values, while with pH values greater than 9 the products can become unstable. Several denaturants, for example, guanidine hydrochloride, were also investigated with the idea to decrease aggregation. A denaturant may, however, play a more significant role in breaking the secondary structure and minimizing aggregation of larger peptide systems during s-tetrazine incorporation. To prevent disulfide formation, adding reducing agents to the reaction solution were investigated. Tris(2-carboxyethyl)phosphine (TCEP) was found both to react with dichlorotetrazine during the course of the reaction and to reduce the s-tetrazine motif once inserted to yield the S,S-dihydrotetrazine congener. Preferred phase-transfer conditions entailed addition of 1a in a fifty millimolar aqueous solution of monosodium phosphate with dichlorotetrazine dissolved in chloroform as a separate phase to furnish 2a, with minimal side-product formation. Good to excellent yields resulted after purification by reverse-phase chromatography.

Example 4: Photochemical Tetrazine Release

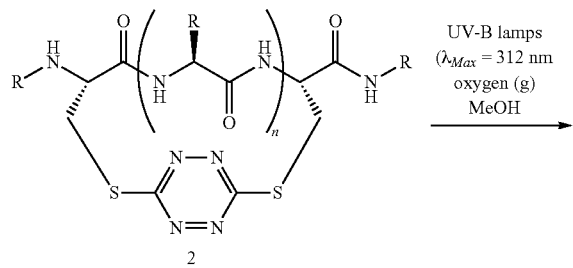

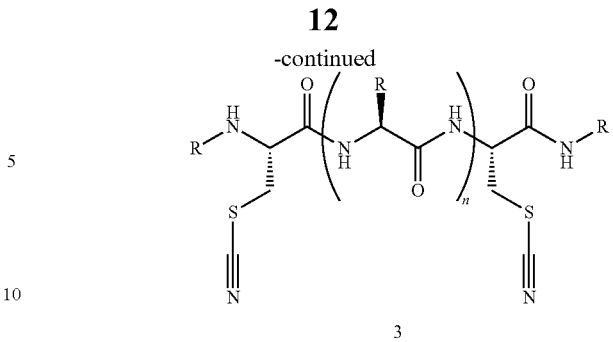

A 10 mL glass vial was charged with a solution of tetrazine peptide 2a in MeOH (1-2 nM). The contents were caped with a septum and sparged with oxygen gas for 15 minutes. The solution as then irradiated in a Rayonet® photoreactor equipped with six (7 watt) UV-B lamps ($λ_{max}$=312 nm) until the solution turned colorless. The MeOH was evaporated in vacuo, then redissolved in water and lyophilized to remove the tetrazine chromophore, to provide dithiocyanate peptide 3a in near quantitative yield as a white amorphous powder, thereby releasing the restricted conformation. Compounds 2b-i were uncoupled using the same protocol to yield compounds 3b-i in FIG. 2.

A similar procedure using twelve (7 watt) UV-A lamps ($λ_{max}$=365 nm) and a thin-walled Pyrex® tube was utilized to prepare compound 3a (96%) as a white amorphous powder. The spectral data for this compound was identical to 3a prepared as described immediately above.

Example 5: Native Peptide Regeneration

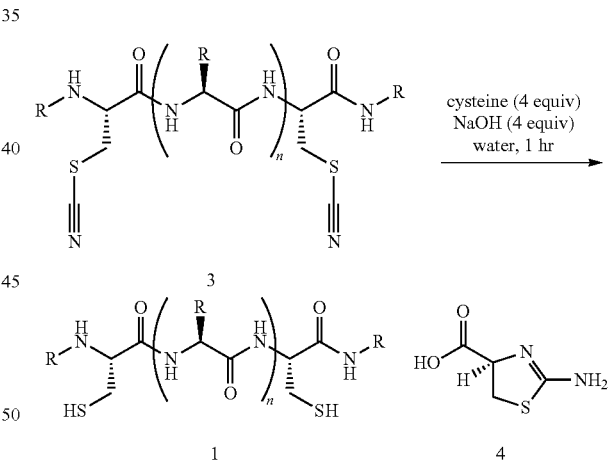

A 13 mm test tube was charged with peptide 3a (6.2 mg, 10 μmol) was dissolved in water (1.0 mL), then a pre-mixed solution of cysteine (121 mg, 1 mmol, 4 equiv) and NaOH (4 mL of 0.25M solution, 1 equiv) was added to peptide 3a. The contents were stirred for 1.0 hour, then formic acid (4 equiv) was added to neutralize the reaction. The crude mixture was then purified by reverse-phase high-pressure liquid chromatography (HPLC) to yield 4.9 mg of 1a (87%). $^1$H NMR (500 MHz, D$_2$O) δ ppm 1.38-1.48 (m, 2H) 1.68 (quin, J=7.28 Hz, 2H) 1.72-1.81 (m, 1H) 1.85-1.94 (m, 1H) 2.19 (q, J=7.27 Hz, 2H) 2.55 (t, J=7.33 Hz, 2H) 2.90-3.02 (m, 6H) 3.89 (t, J=4.95 Hz, 2H) 4.14 (t, J=6.54 Hz, 1H) 4.32 (dd, J=8.92, 5.15 Hz, 1H) 4.52 (t, J=5.45 Hz, 1H) 4.58 (t, J=6.24 Hz, 1H) 4.61 (t, J=6.30 Hz, 1H). $^{13}$C NMR (126

MHz, D$_2$O) δ 176.6, 176.2, 171.6, 171.5, 171.4, 169.4, 61.1, 55.8, 55.7, 55.6, 53.4, 52.4, 39.3, 30.3, 29.4, 26.3, 26.1, 25.5, 25.4, 22.2. HRMS (ES) found m/z 569.2067 [(M+H)$^+$; calcd for C$_{20}$H$_{37}$N$_6$O$_9$S$_2$: 569.2063].

Compounds 1b-e and h were prepared using the above procedure, and varying the amounts of peptides 3b-e and h (1-5 mg) and formic acid (4-8 equiv). See, FIG. 3.

Example 6: Stapling and Unstapling of Thioredoxin

Protocol A.

The enzyme thioredoxin, an oxidoreductase, well known to possess a single solvent exposed disulfide bond, was subjected to the methods of the disclosure. To this end, thioredoxin was dissolved in a phase-transfer buffer and treated with immobilized a reducing agent [tris(w-carboxyethyl)phosphine (TCEP)] to reduce the disulfide linkage. The resultant filtrate containing the reduced protein was then used directly in the phase-transfer reaction to insert the s-tetrazine chromophore between Cys32 and Cys35. The lyophilized product displayed the typical red color of tetrazine, a qualitative indicator for s-tetrazine incorporation. Additionally, matrix-assisted laser desorption/ionization (MALDI) analysis revealed a +78 m/z shift in mass equal to the s-tetrazine chromophore. Photolysis of the tetrazine stapled enzyme led to removal of the s-tetrazine chromophore, which in turn permitted reductive removal of the cyanide groups with cysteine to return to the native protein thioredoxin.

Protocol B.

To a 1.7 mL mini-centrifuge tube containing thioredoxin (0.25 mg, 21 nmol) dissolved in acetate buffer pH 5 (200 mM, 100 µL), was added TCEP immobilized on agrose (300 µL, 8 µmol/mL, 2.4 µmol, 112 equiv); the final buffer concentration was 50 mM. The reaction was stirred at room temperature for 2 hours under an argon atmosphere. The contents were kept under a blanket of argon, then filtered through a plastic pipet tip with a cotton plug and rinsed with degassed 50 mM acetate buffer pH 5 (3×200 µL). To the pooled filtrates (1.0 mL) in a 1.7 mL mini-centrifuge tube was added a pre-mixed solution of dichlorotetrazine in DMSO (20 µL, 87 nmol, 4 equiv, 0.67 mg/mL) and stirred for 1 minute. The solution was then transferred to a pre-equilibrated disposable PD-10 desalting column and eluted with 50 mM Tris, pH 7.8, 150 mM NaCl. The fractions containing protein were pooled and stored at 4° C. MALDI-TOF m/z 11757.782 [(M+H)+; 11756.45; calculated for Trx-1 (11675.43 Da)+tetrazine (80.01 Da)+H+(1.01)]. See FIG. 5.

Comparison Sample

A sample of tetrazine thioredoxin (0.1 mg, 8 nmol), from the desalting column in 50 mM Tris, pH 7.8, 150 mM NaCl (1000 µL) was divided between two 1.7 mL mini-centrifuge tubes. One sample underwent photolysis and the other used as a comparison.

Tetrazine Thioredoxin Photolysis

A 1.7 mL mini-centrifuge tube containing tetrazine thioredoxin (0.05 mg, 4 nmol) dissolved in 50 mM Tris, pH 7.8, 150 mM NaCl (500 µL) was suspended in a Rayonet® photoreactor equipped with three UV-B lamps. The contents were irradiated for 1 hour, MALDI indicated consumption of the starting material with partial loss of the nitrile groups.

Regeneration of Native Protein

To the photolyzed sample dissolved in 50 mM Tris, pH 7.8, 150 mM NaCl (500 µL), was added cysteine (25 µL) of a 20 mM solution in the Tris buffer system and TCEP (25 µL) of a 20 mM solution in the Tris buffer system. The contents were allowed to stand for 4 hours and then diluted to 3 mL with the Tris buffer system and transferred for centrifugation in an Amicon centrifugal filter (MWCO 3000, 35° fixed angle rotor @ 7000×G, 30 minutes, 4° C.), the concentrated sample (150 µL) was diluted to 3 mL and repeated. The retenate was collected and diluted to 500 µL with the Tris buffer system, then Ellman's reagent [5,5'-dithio-bis-(2-nitrobenzoic acid)] (25 µL of a 20 mM solution in the Tris buffer system) was added and allowed to stand for 6 hours. The contents were then diluted to 3 mL with the Tris buffer system and transferred for centrifugation in an Amicon centrifugal filter (MWCO 3000, 35° fixed angle rotor @ 7000×G, 30 minutes, 4° C.). The retenate was collected and diluted to 500 µL with the Tris buffer solution and analyzed by MALDI-TOF and FPLC: MALDI-TOF m/z 11676.188 [(M+H)+; 11676.44].

Fast protein liquid chromatography (FPLC) was conducted with an AKTA FPLC equipped with a P 920 pump and UPC-900 control box. Proteins were separated with a Superdex 75/10/300 column at 4° C. and eluted with 50 mM Tris, pH 7.8, 150 mM NaCl (isocratic) at 0.5 mL/min. Approximated extinction coefficient (ε) values were calculated for thioredoxin (Trx) and tetrazine-thioredoxin (tet-Trx). The Trx protein contains 2 Trp and 2 Tyr residues, the ε values used in the calculations are listed below.

| Residue | Extinction Coefficient (ε) Used (cm$^{-1}$M$^{-1}$) |
|---|---|
| Tyrosine | 1280 |
| Trytophan | 5690 |
| S,S-tetrazine | 11369 |

$$\epsilon_{Trx} = (2 \times 5690 \text{ cm}^{-1}\text{M}^{-1}) + (2 \times 1280 \text{ cm}^{-1}\text{M}^{-1}) = 13940 \text{ cm}^{-1}\text{M}^{-1}$$

$$\epsilon_{tet-Trx} = (2 \times 5690 \text{ cm}^{-1}\text{M}^{-1}) + (2 \times 1280 \text{ cm}^{-1}\text{M}^{-1}) + (11369 \text{ cm}^{-1}\text{M}^{-1}) = 25309 \text{ cm}^{-1}\text{M}^{-1}$$

| Residue | Extinction Coefficient (ε) Used (cm$^{-1}$M$^{-1}$) |
|---|---|
| Threodoxin | 13940 |
| Tetrazine-Trx | 25309 |

The measured areas from FPLC chromatograms are:

| Residue | Area of Peaks at 13 mins (mAU/mL) |
|---|---|
| Tetrazine-Trx | 19.11 |
| Regenerated-Trx | 8.92 |

The measured tetrazine-thioredoxin absorbance ($A_{meas}$) was normalized ($A_{norm}$) to account for the extinction coefficient contributed by the tetrazine to permit comparison with the regeneration thioredoxin using the equation below.

$$A_{norm} = \frac{A_{meas} \varepsilon_{Trx}}{\varepsilon_{tet-Trx}} = \frac{19.11 \text{ mAU} * \text{mL}^{-1} * 13940 \text{ cm}^{-1} M^{-1}}{25309 \text{ cm}^{-1} M^{-1}} = 10.53 \text{ mAU} * \text{mL}^{-1}$$

The regenerated thioredoxin yield was calculated using the equation below.

$$\frac{A_{regen-Trx}}{A_{norm-Trx}} \frac{8.92 \text{ mAU} * \text{mL}^{-1}}{10.53 \text{ mAU} * \text{mL}^{-1}} \times 100\% = 84.7\%$$

The FPLC chromatograms of the regenerated thioredoxin and normalized tetrazine thioredoxin were overlaid for comparison. The calibration curve was used to approximate molecular weight which indicated a monomer/dimer system. The yield of the regenerated thioredoxin was also found to be ~80%, relative to the normalized tetrazine thioredoxin after calculating the measured areas from the FPLC chromatograms.

Example 7: Tetrazine Functionalization nyl) carbonate was prepared as described in Schieber, Christine; Bestetti, Alessandra; Lim, Jet Phey; Ryan, Anneke D.; Nguyen, Tich-Lam; Eldridge, Robert; White, Anthony R.; Gleeson, Paul A.; Donnelly, Paul S.; Williams, Spencer J.; Mulvaney, Paul Angew. Chem. Int. Ed. 2012, 51(42) p. 10523-10527.

To a 5 mL round bottom flask containing 5-(2-aminoethyl)carbamoyl)-2-(6-hydroxy-3-oxo-3H-xanthen-9-yl) benzoic acid (9.0 mg, 22 μmol) dissolved in MeCN (500 μL) was added bicyclo[6.1.0]non-4-yn-9-ylmethyl(4-nitrophenyl) carbonate (8.3 mg, 26 μmol, 1.2 equiv) in MeCN (250 μL) followed by the addition of pyridine (16 μL, 200 μmol, 10 equiv) and DMAP (2.7 mg, 22 μmol, 1 equiv). The contents were then stirred at 35° C. for 48 hours. The reaction mixture was evaporated and the crude re-dissolved in water/MeCN (7:3, 1000 μL) and purified by reverse-phase HPLC (gradient 10-80% organic over 15 minutes) to give 8.2 mg (63%) of 5-((2-(((((1R,8S,9R)-bicyclo[6.1.0]non-4-

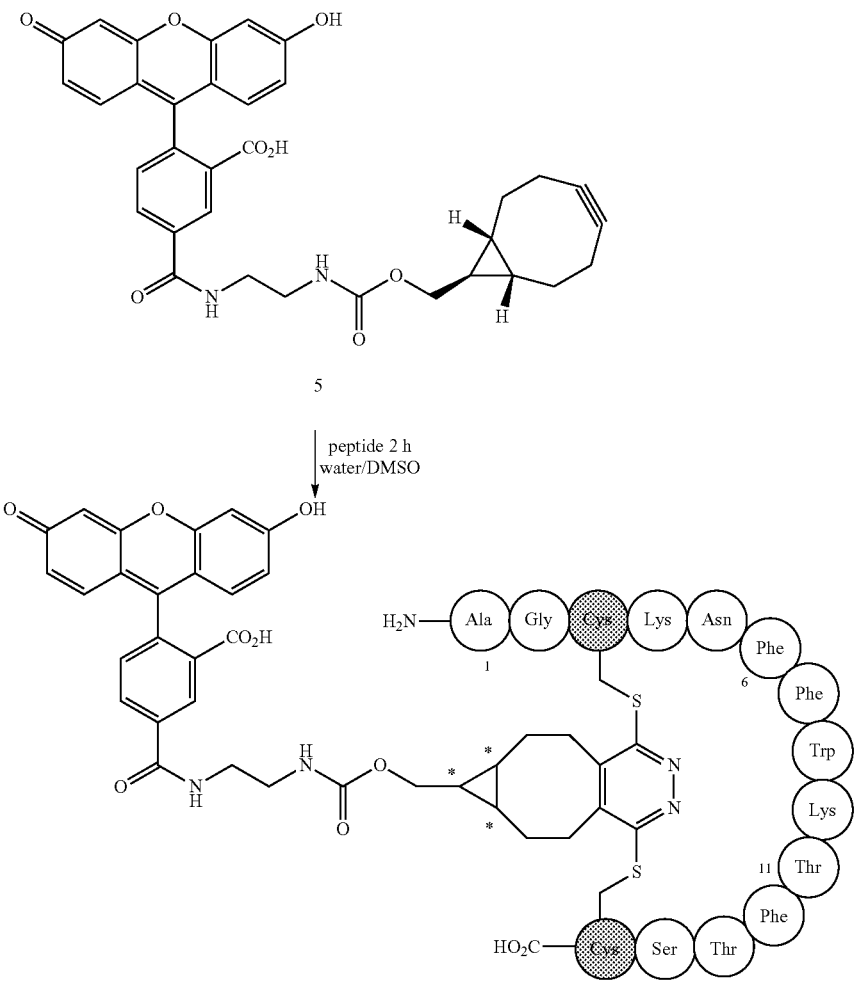

Starting material 5-(2-aminoethyl)carbamoyl)-2-(6-hydroxy-3-oxo-3H-xanthen-9-yl)benzoic acid was prepared as described in Gasparini, G.; Bang, E. K.; Molinard, G.; Tulumello, D. V.; Ward, S.; Kelley, S. O.; Roux, A.; Sakai, N.; Matile, S. J. Am. Chem. Soc. 2014, 136, 6069-6074 and (1R,8S,9R)-bicyclo[6.1.0]non-4-yn-9-ylmethyl(4-nitropheyn-9-yl)methoxy)carbonyl)amino)ethyl)carbamoyl)-2-(6-hydroxy-3-oxo-3H-xanthen-9-yl)benzoic acid after lyophilization. HRMS (ES) m/z 595.2069 [(M+H)+; calcd for $C_{34}H_{31}N_2O_8$: 595.2080]. $^1$H NMR (500 MHz, Methanol-d$_4$) δ 8.49 (s, 1H), 8.21 (d, J=8.0 Hz, 1H), 7.34 (d, J=8.0 Hz, 1H), 6.79 (s, 2H), 6.73 (d, J=8.3 Hz, 2H), 6.64 (d, J=8.8

Hz, 2H), 4.15 (d, J=8.2 Hz, 2H), 3.54 (t, J=5.7 Hz, 2H), 3.39 (t, J=6.0 Hz, 2H), 2.19 (d, J=12.8 Hz, 4H), 2.09 (d, J=15.3 Hz, 2H), 1.56 (dd, J=21.8, 9.7 Hz, 2H), 1.36 (dt, J=17.3, 8.6 Hz, 1H), 0.87 (t, J=10.0 Hz, 2H).

To a 5 mL round bottom flask was added a solution (1.1 mM) of peptide 2h dissolved in water (500 μL) followed by a solution (1.2 mM) of bicyclononyne 5 in DMSO (500 μL). The contents were stirred at room temperature for 4 days and the solvent removed in vacuo. The residue was purified by reverse-phase HPLC (gradient 10-60% organic over 15 min) to give (0.9 mg, 68%) of a yellow-orange powder after lyophilization. MALDI-TOF m/z 2283.468 [(M+H)+; calcd for $C_{112}H_{135}N_{22}O_{27}S_2$: 2283.930].

Figure 5:
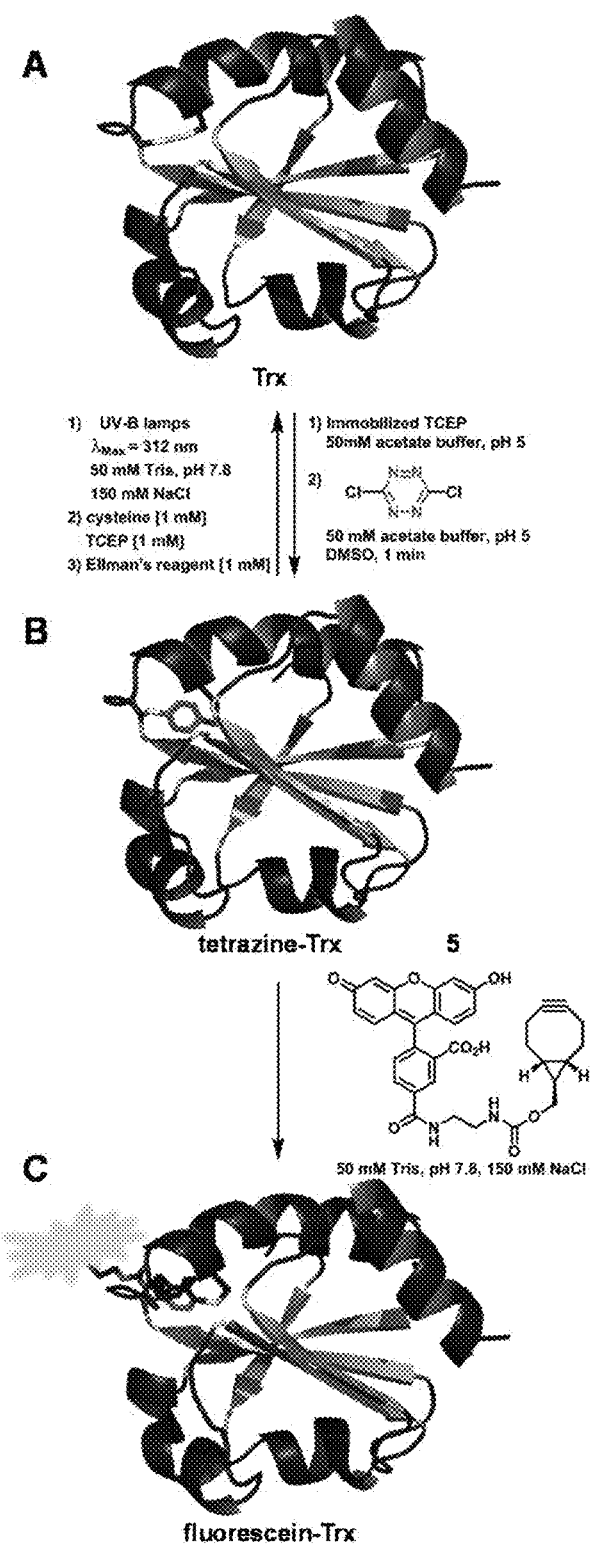
FIG. 5 depicts one embodiment of the invention using thioredoxin protein

Example 8: Inverse-Electron Demand Diels-Alder Reaction of Bicyclononyne with Tetrazine Thioredoxin To demonstrate the introduction of probes exploiting inverse electron demand Diels-Alder reactions, fluorescein dye 5 was prepared as described above. To a 1.7 mL mini-centrifuge tube containing tetrazine thioredoxin (0.05 mg, 4 nmol) dissolved in 50 mM Tris, pH 7.8, 150 mM NaCl (500 μL) was added a solution of compound 5 (100 μL, 0.024 mg, 40 nmol, 10 equiv) dissolved in the Tris buffer system. The contents were allowed to stand at ambient temperature for 10 days. The contents were next transferred for centrifugation in an Amicon centrifugal filter (MWCO 3000, 35° fixed angle rotor @ 7000×G, 30 minutes, 4° C.), the concentrated sample (150 μL) was diluted to 3 mL with the Tris buffer and repeated. The reaction was monitored by mass spectrometry, which illustrated the loss of nitrogen and an additional mass equal to 5. MALDI-TOF m/z 12323.622 [(M+H)+; 12322.64; calculated for tetrazine Trx (11755.44)+5 (594.20 Da)+H+(1.01)—$N_2$ (28.01)]. A diastereomeric mixture of the fluorescein labeled peptide 6 was obtained (FIG. 5).

---

What is claimed:

1. A process comprising:
   preparing a phase-transfer reaction medium comprising
   an aqueous solution of an unprotected amino acid sequence comprising two proximal cysteine residues or two homocysteine residues; and
   an organic solution of a di-halo-tetrazine;
   contacting the aqueous solution with the organic solution for a time sufficient to form an S,S-tetrazine moiety;
   irradiating the S,S-tetrazine moiety with light to form an amino acid sequence comprising two proximal thiocyanate moieties; and
   contacting the amino acid sequence comprising two proximal thiocyanate moieties with cysteine for a time sufficient to produce the amino acid sequence comprising two proximal cysteine residues or the amino acid sequence comprising two proximal homocysteine residues;
   wherein the proximal cysteine residues, the proximal homocysteine residues, and the proximal thiocyanate moieties are separated by 0 to 35 amino acid residues.

2. The process of claim 1, wherein each amino acid sequence is a peptide, a protein, or a protein fragment.

3. The process of claim 1, wherein the aqueous solution has a pH of from about 5 to about 9.

4. The process of claim 1, wherein the aqueous solution further comprises a buffer.

5. The process of claim 4, wherein the buffer is monosodium phosphate or guanidine hydrochloride.

6. The process of claim 1, wherein the organic solution comprises chloroform, ethyl acetate, diethyl ether, toluene, dichloromethane, cyclohexane, or a combination thereof.

7. The process of claim 6, wherein the organic solution comprises chloroform.

8. The process of claim 1, wherein the organic solution has a solubility in water of less than 10 g/mL at 20° C.

9. The process of claim 1, wherein the proximal cysteine residues, the proximal homocysteine residues, and the proximal thiocyanate moieties are separated by 1, 2, 3, 4, 5, 10, or 27 amino acid residues.

10. The process of claim 1, wherein the di-halo-tetrazine is dichlorotetrazine.

11. The process of claim 1, wherein the irradiation is with UV-A light or UV-B light.

12. The process of claim 1, wherein the step of contacting the amino acid sequence comprising two proximal thiocyanate moieties with cysteine occurs in aqueous solution.

13. The process of claim 1, wherein the pH of the aqueous solution is a basic pH.

14. The process of claim 1, wherein the amino acid sequence includes at least 4 amino acid residues.

15. The process of claim 1, wherein the amino acid sequence includes at least 6 amino acid residues.

* * * * *